United States Patent [19]

Linnecke

[11] Patent Number: 5,388,392
[45] Date of Patent: Feb. 14, 1995

[54] APPARATUS FOR POWDER FILLING ANTIBODY TESTING DEVICES

[75] Inventor: Carl Linnecke, Arcadia, Calif.

[73] Assignee: V-Tech, Inc., Pomona, Calif.

[21] Appl. No.: 956,308

[22] Filed: Oct. 5, 1992

[51] Int. Cl.⁶ .................. B65B 1/24; B65B 29/10; B30B 11/00
[52] U.S. Cl. .................. 53/527; 53/282; 53/900
[58] Field of Search ............. 53/527, 900, 281, 471, 53/438, 129.1, 282, 284.5; 422/101

[56] References Cited

U.S. PATENT DOCUMENTS

| | | | |
|---|---|---|---|
| 3,070,932 | 1/1963 | Höfliger | 53/281 |
| 3,554,412 | 1/1971 | Hayashi et al. | 53/900 X |
| 4,959,943 | 10/1990 | Yamamoto et al. | 53/900 X |
| 4,964,262 | 10/1990 | Moser et al. | 53/900 X |

FOREIGN PATENT DOCUMENTS

| | | | |
|---|---|---|---|
| 0049909 | 4/1982 | European Pat. Off. | 53/900 X |
| 290611 | 11/1931 | Italy | 53/900 X |

Primary Examiner—James F. Coan
Attorney, Agent, or Firm—Drucker & Sommers

[57] ABSTRACT

An apparatus for assembling antibody testing devices for use in conducting biotests which utilize a powder fluid absorbing material to fill the housing of the antibody testing devices. The apparatus has several stations at which the various assembly steps take place. At the first station, lower housing portions of the antibody testing device are loaded onto a conveyor belt. At a second station, the lower housing portions are loaded with a fluid absorbing powder. At a third station, the powder loaded lower housing portions are engaged with a slotted indexing carousel wheel and are carried away from the conveyor belt. At a fourth station, the liquid absorbing powder in the lower housing portion is compressed therein. At a fifth station, a disk of filter material is placed atop the liquid absorbing powder loaded into the housing portion. At a sixth station, caps carrying membranes which have been spotted with receptors are engaged with the powder filled housing portion. At a seventh station, the assembled antibody testing devices are disengaged from the slotted indexing carousel wheel and are returned to the conveyor belt. At an eight station, the assembled antibody testing devices are vacuumed free of any powder which may have collected there. At a ninth station, the slotted indexing carousel wheel is forced into precise alignment such that its slots are aligned with the other stations located therearound.

16 Claims, 4 Drawing Sheets

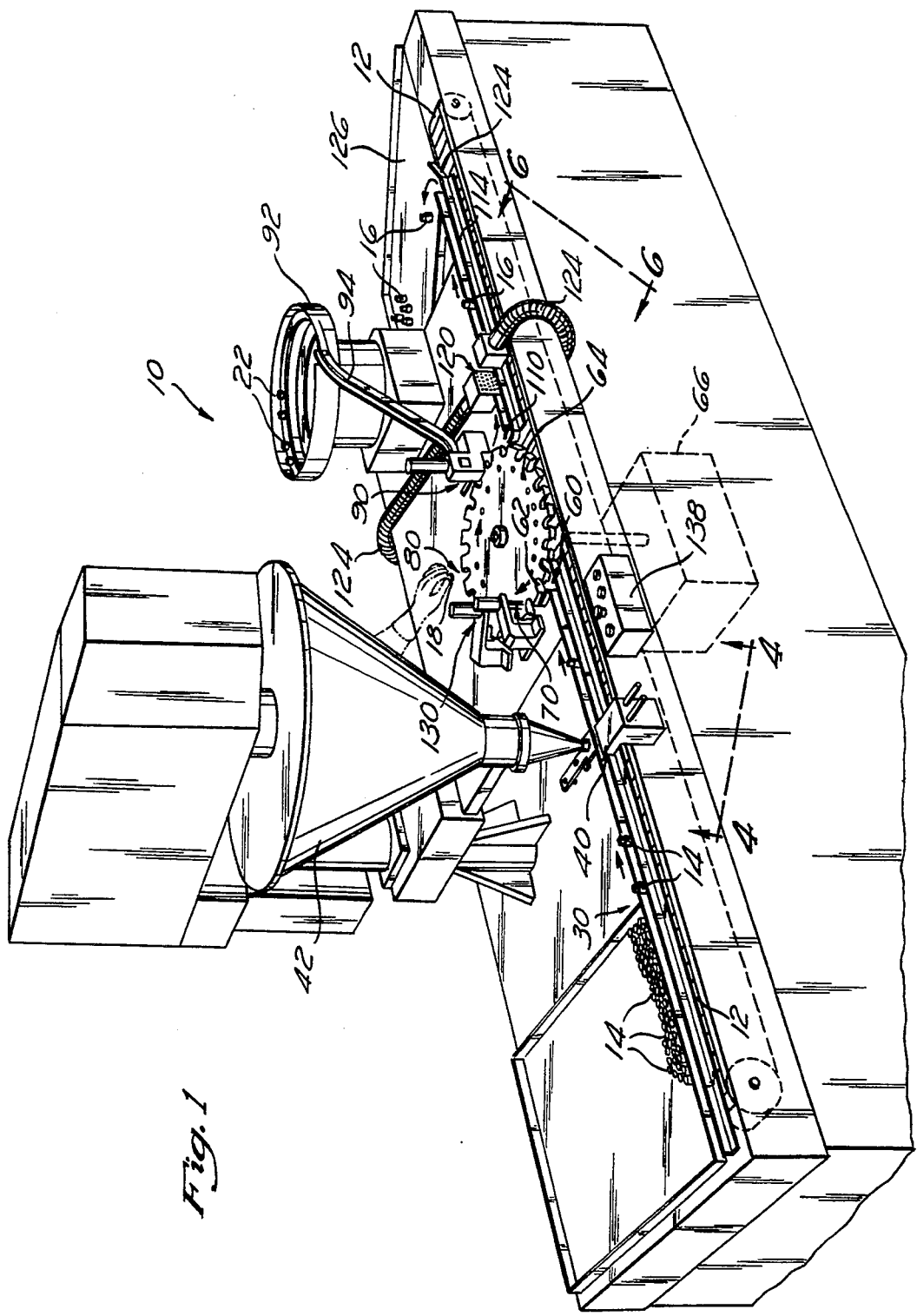

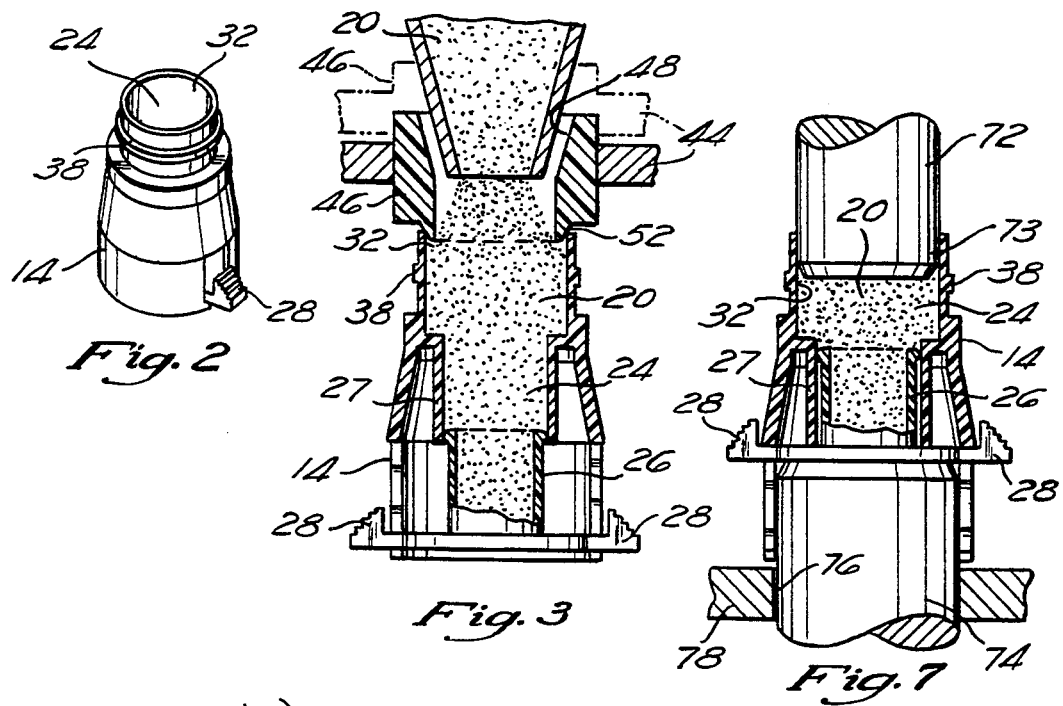
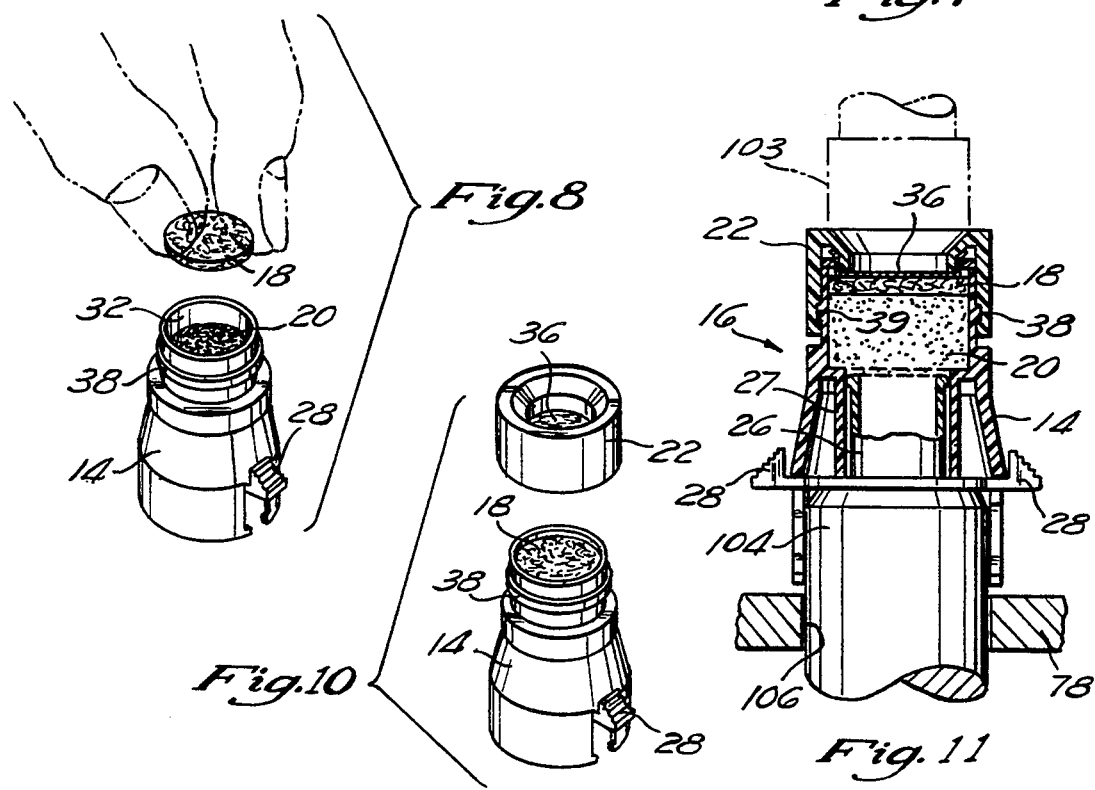

5,388,392

APPARATUS FOR POWDER FILLING ANTIBODY TESTING DEVICES

BACKGROUND OF THE INVENTION

1. Field of the Invention

The invention relates to the field of apparatuses for assembling antibody testing devices, particularly apparatuses which can be used to assemble antibody testing devices which are to be filled with liquid absorbing powder.

2. Description of the Prior Art

In the past, antibody testing devices, such as those of U.S. Pat. No. 4,789,526 to Matkovich and U.S. Pat. No. 4,797,260 to Parker, have included porous filter plugs in their housing portions to absorb the fluid samples used with these antibody test devices. These porous filter members are commonly made of fibrous materials, such as cellulose acetate. However, due to the relatively low absorbency of these prior art materials, only small volumes of fluids can be used with these devices. In co-pending U.S. application Ser. No. 07/695,950, there is disclosed an antibody test device which includes a hydrophilic liquid absorbing powder material, such as diatomaceous earth, in lieu of a porous fibrous filter plug member. Since the powder material is more absorbent than the previously used porous fibrous materials, greater volumes of fluid samples can be used for an antibody testing device of a given size, thereby permitting these antibody testing devices to be employed in biotests for which these devices were previously not useable, due to the relatively large volume of fluid sample required.

However, until now, there has not been available an apparatus for economically and precisely filling antibody test devices with hydrophilic liquid absorbing powders on a commercial scale, due to the difficult of handling the powder material.

SUMMARY OF THE INVENTION

The invention disclosed herein provides an apparatus for assembling antibody test devices which include hydrophilic powder as the fluid absorbing means.

One aspect of the invention is an apparatus for assembling the components of an antibody testing device, utilizing powder as a fluid absorbing means, into a completed antibody testing device, comprising a station at which a lower housing portion is filled with a fluid absorbing powder, and a station at which a membrane carrying cap portion of the antibody testing device is engaged with said lower housing portion to complete the assembly of the antibody testing device.

Another aspect of the invention is an apparatus for assembling the components of a antibody testing device utilizing powder as a fluid absorbing means into a completed antibody testing device, comprising:

(a) a first station at which a lower housing portion of the antibody testing device is placed on said apparatus;

(b) a second station at which said lower housing portion is filled with a liquid absorbing powder;

(c) a third station at which said housing portion is engaged with a slot on a slotted indexing carousel wheel;

(d) a fourth station at which said liquid absorbing powder in said lower housing portion of said antibody testing device is compressed into said lower housing portion;

(e) a fifth station at which a filter disk is placed atop said compressed liquid absorbing powder loaded in said lower housing portion;

(f) a sixth station at which a membrane carrying cap portion of the antibody testing device is engaged with said lower housing portion to complete the assembly of the antibody testing device; and (g) a seventh station at which said assembled antibody testing device is disengaged from said slotted indexing carousel wheel.

BRIEF DESCRIPTION OF THE DRAWINGS

The invention is described below in greater detail with reference to the drawings.

FIG. 1 is a perspective view showing the apparatus for assembling antibody testing devices including a fluid absorbing powder.

FIG. 2 is a perspective view of the lower housing portion of the antibody testing device which is placed on the conveyor belt at the first station.

FIG. 3 is a cross-sectional view of the lower housing portion of FIG. 2 being filled with liquid absorbing powder at the second station.

FIG. 7 is a partial cross-sectional view showing the fourth station of the apparatus at which the liquid absorbing powder is compressed into the lower housing portion of the antibody testing device.

FIG. 8 is a perspective view showing how a disk of filter material is placed atop powder loaded in a lower housing portion of the antibody testing device at the fifth station.

FIG. 10 is an exploded view of the antibody testing device assembled by the apparatus, showing the antibody carrying cap and the powder filled lower housing portion thereof.

FIG. 11 is a cross-sectional view showing the antibody carrying cap and powder filled housing being snapped together at the sixth station.

DESCRIPTION OF THE PREFERRED EMBODIMENTS

Figure 4:
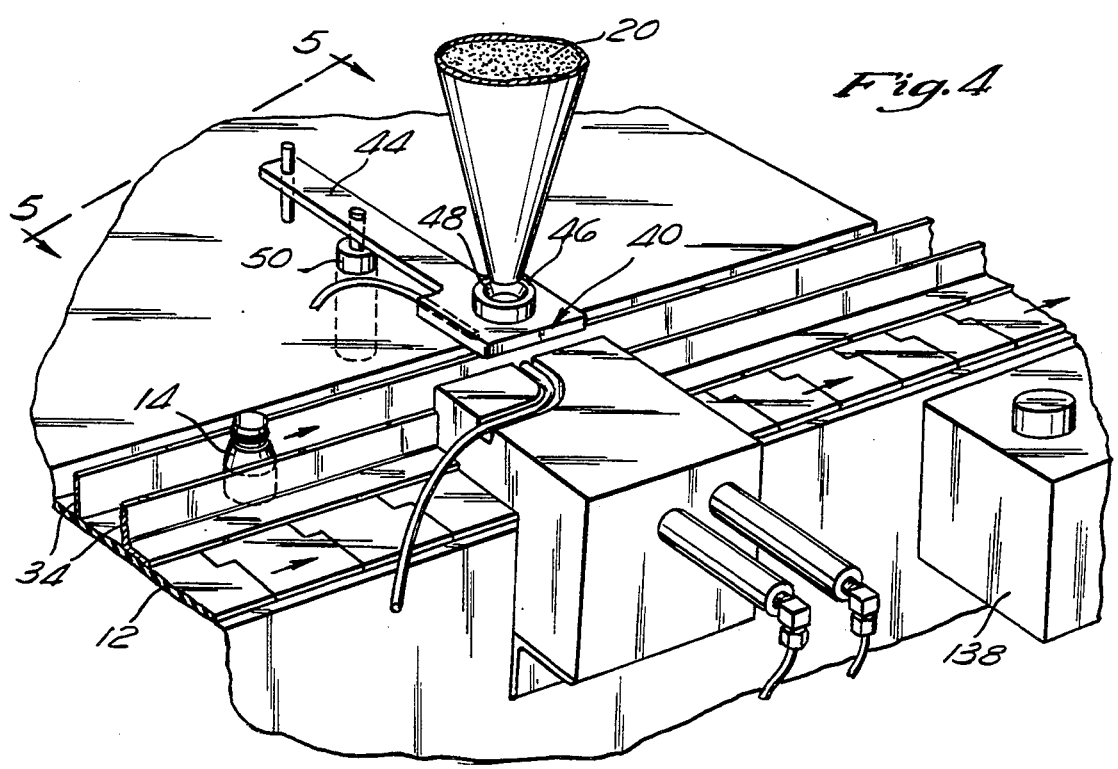
FIG. 4 is a front perspective view of the second station.

Referring first to FIG. 1, a perspective overview of the apparatus 10 is shown. The apparatus 10 includes a conveyor belt 12 which conveys the lower housing portion 14 (See FIG. 2) of an antibody testing device 16 (See FIG. 11) from a first station 30, wherein the lower housing portion 14 of the antibody testing device 16 are placed on the conveyor belt 12, to a second station 40, where the lower housing portion 14 is filled with a liquid absorbing powder by an automated powder delivery device 42. After being filled at the second station 40, the powder filled lower housing portion 14 is transported down the conveyor belt 12 to a third station 60, at which it engages with one slot 62 on a slotted indexed carousel wheel 64. The slotted indexing carousel wheel 64 is rotated in predetermined steps by a stepper motor and its gearing 66 and transports the powder filled lower housing portion 14 to a fourth station 70, wherein the powder is compressed into the lower housing portion 14. At a fifth station 80, a filter disk 18 is placed on top of the compressed powder 20 in the lower housing portion 14. At a sixth station 90, the cap 22 of the antibody testing device 16 is snappedly engaged with the powder filled lower housing portion 14 to complete the assembly of the antibody testing device 16. At a seventh station 110, the assembled antibody test device 16 is disengaged from the rotating slotted indexing carousel wheel 64 and is returned to the conveyor belt 12. At the eight station 120, any powder which may have fallen on the outside of the assembled antibody testing device 16 is vacuumed off. At a ninth station 130, the rotating slotted indexing carousel wheel 64 is forced into precise alignment with the other stations.

Having described the various portions and stations of the apparatus 10 and the parts of the antibody testing device 16 assembled thereon in overview, these various portions and stations and parts of the antibody testing device 16 will now be described in greater detail.

Referring to FIGS. 1 and 4, at the first station 30, the lower housing portions 14 of the antibody testing device 16 are placed between a pair of spaced apart guide walls 34 which are positioned to lie spaced over the continuously moving conveyor belt 12. As presently embodied, manual placement of the lower housing portion 14 of the device 16 on the conveyor belt by a human operator is contemplated. However, this step could be accomplished in an automated manner by utilizing a vibratory sorter to automatically fed the lower housing portions 14 to the conveyor belt 12 by a declined track, or by other known means.

Figure 5:
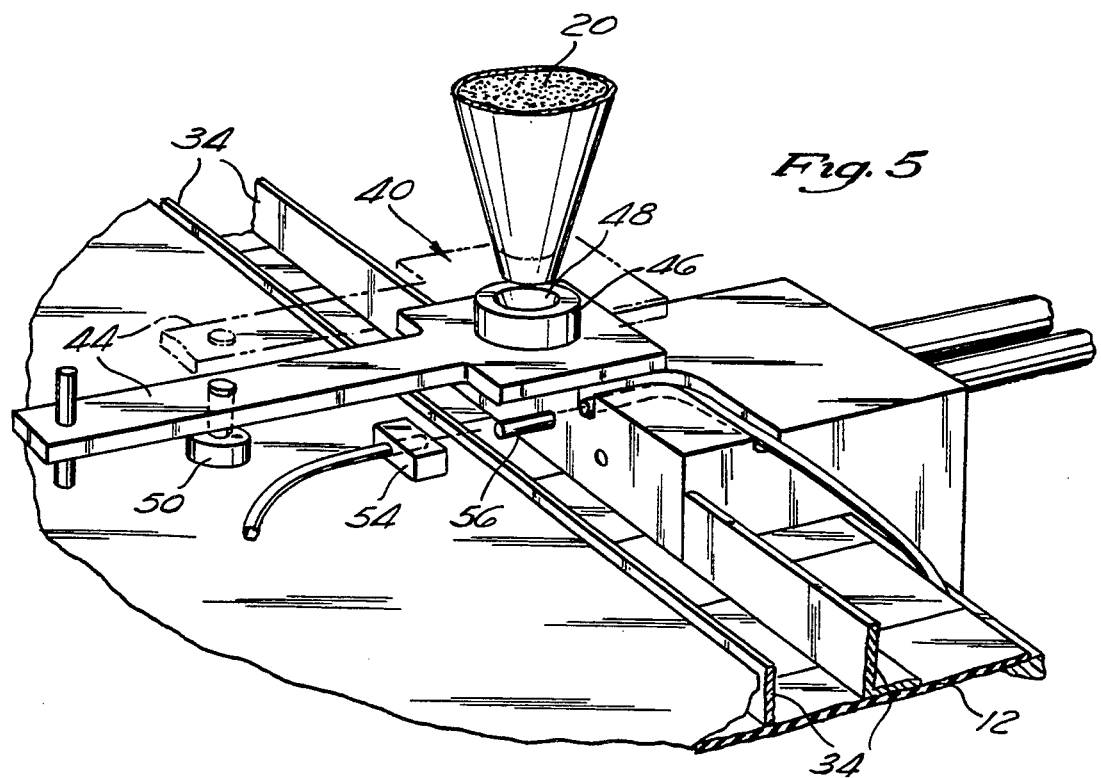
FIG. 5 is a rear perspective view of the second station, taken along lines 5—5 of FIG. 4.

The continuously moving conveyor belt 12 moves the lower housing portion 14 to the second station 40, shown in FIGS. 3–5, wherein a predetermined quantity of liquid absorbing powder 20 is automatically fed from a commercially available automatic powder filling machine 42 into the interior cavity 24 of the lower housing portion 14 of the antibody testing device 16. The applicant uses an auger powder filling machine 42, by All-Fill, of Exton, Pa. with a computer control unit to deliver the desired volume and weight of liquid absorbing powder to the lower housing portion 14. As is shown in FIG. 3, the lower housing portion 14 has a piston portion 26 with a cavity which is also filled up with the liquid absorbing powder 20 and allow the piston portion 26 to be moved up and down in a cylinder portion 27 of the lower housing portion 14. A pair of finger grips 28 are integral with the piston portion 26. The second station 40 has a pneumatically operated lifting arm 44. The lifting arm 44 carries at one end a funnel sleeve 46 which is positioned directly over the open mouth 32 of the lower housing portion 14. The funnel sleeve 46 has a funneled top 48 which helps direct the liquid absorbing powder 20 into the lower housing portion 14. The lifting arm 44 can be moved pneumatically by a pneumatic piston 50 between a raised position (shown in phantom lines) and a lowered position (shown in solid lines). As shown in FIG. 3, when the lifting arm 44 and its carried funnel sleeve 46 are moved to the lowered position, a bottom portion 52 of the funnel sleeve 46 will seat with the open mouth 32 of the lower housing portion 14. The liquid absorbing powder 20 is then released into the lower housing portion 14 to fill same. An optical sensor 54 located at the second station 40 indicates the presence or absence of a lower housing portion 14 at the second station 40, and activates a pneumatically operated barrier arm 56 to block the movement of the lower housing portion 14 on the conveyor belt 12 during the powder filling sequence. After the lower housing portion 14 is filled with powder 20, the barrier arm 56 is temporarily withdrawn, and the powder filled lower housing portion 14 will be free to continue to travel on the conveyor belt 12 to the third station 60. Another lower housing portion 14 will then be prepared for loading with liquid absorbing powder.

Figure 6:
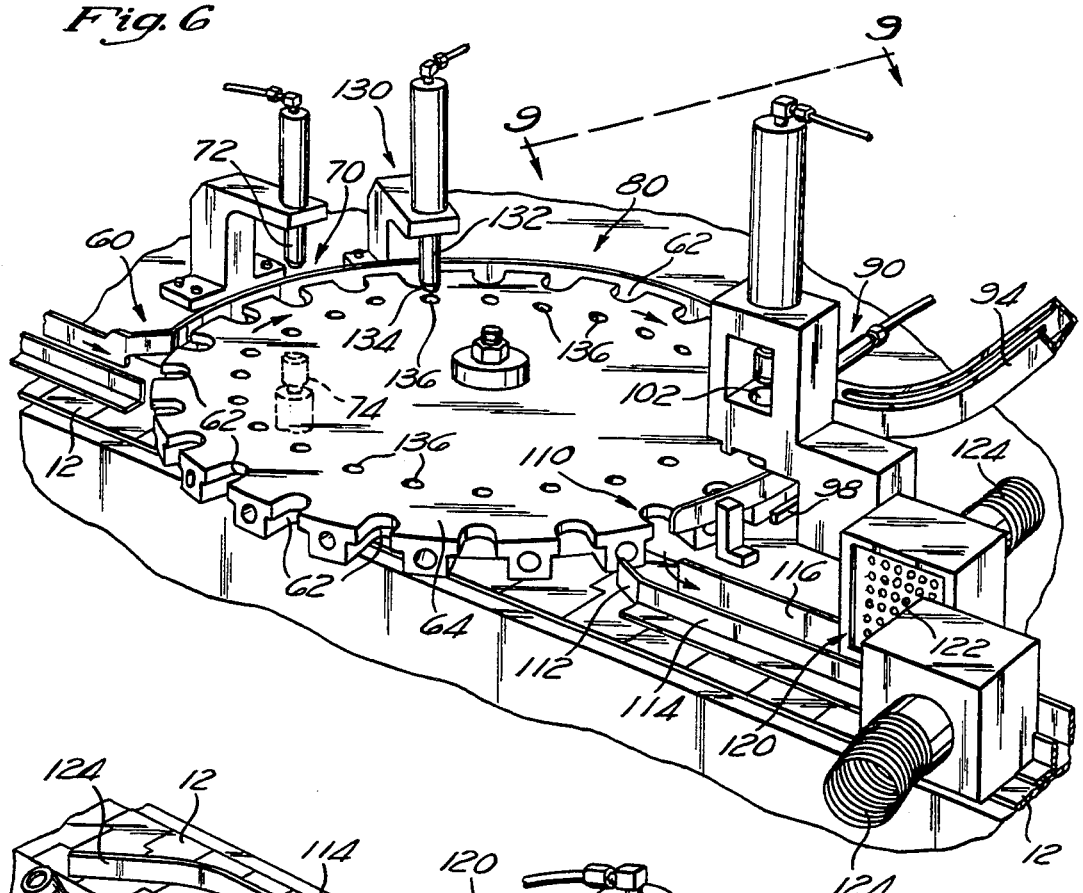
FIG. 6 is a perspective view of the slotted indexing carousel wheel of FIG. 1 showing the various stations located therearound.

Referring now to FIG. 6. at the third station 60, the powder loaded lower housing portion 14 will engage with a slot 62 in the slotted indexing carousel wheel 64, which is aligned to receive the powder loaded lower housing portion 14 as it travels down the conveyor belt 12. The slotted indexing carousel wheel 64 is rotated in precise steps by a stepper motor and its gearing 66, shown in FIG. 1, to advance the slotted indexing carousel wheel 64 by one slot 62 for each sequence of operation of the apparatus 10.

After the powder loaded lower housing portion 14 is engaged with the slot 62, the indexing carousel wheel 64 is advanced forward in a clockwise direction by one slot 62 (as shown by direction arrows) to ready the adjacent empty slot 62 to accept the next powder loaded housing 14, and to advance the powder loaded lower housing 14 for further assembly steps at downstream stations.

Referring to FIGS. 6 and 7, at the fourth station 70, the powder 20 loaded in the lower housing portion 14 is compressed down into the interior cavity 24 of the lower housing portion 14 by the action of a first pneumatically operated compression piston 72, which has a head 73 which is sized to fit into the open mouth 32 of the lower housing portion 14 to press the powder 20 down into the cavity 24 of the lower housing portion 14 from the top, and a second pneumatically operated raising piston 74, which pushes upwardly through an opening 76 in table top surface 78, thereby pushing the piston portion 26 and its finger grips 28 of the antibody testing device 16 upwardly. The action of the compression piston 72 and the raising piston 74 tightly compress the powder 20 in the interior cavity 24 of the lower housing portion 14.

Referring to FIGS. 1 and 8, the powder loaded lower housing portion 14 is then advanced on the slotted indexing carousel wheel 64 to the fifth station 80, wherein a disk 18 made of filter material such as cellulose acetate, is placed on top of the powder 20 loaded in the lower housing portion 14. As presently embodied, the apparatus 10 relies on manual placement of these filter disk 18 by an human operator at the fifth station 80, but if desired, this station can be automated by the use of a device, such as that disclosed in U.S. Pat. No. 5,036,569 to Linnecke.

Referring to FIGS. 1, 6, 9 and 11, at the sixth station 90, the cap portion 22 of the antibody testing device 16 is snappedly engaged with the powder filled and filter disk covered lower housing portion 14 present there. A properly oriented cap portion 22 is fed from a vibratory feeder 92 down a declining rail 94 to a cap platform 96. Such vibratory feeders and decline rail feeding systems are disclosed in U.S. Pat. No. 5,036,569 to Linnecke. The weight of a plurality of caps portions 22 (not shown) carried in the declining rail 94 will push the lowermost cap portion 22 onto the cap platform 96. A sensor 98 located at the sixth station 90, such as a micro switch on a spring loaded bar, indicates the presence of a powder filled lower housing portion 14 at the sixth station 90. When a powder filled lower housing portion 14 is present at the sixth station 90, a pneumatic pushing arm 100 will push the cap portion 22 sitting on the cap platform 96 forwardly, so that it drops through an opening 102 in the cap platform 96 and land directly on the powder filled lower housing portion 14 located therebelow (not shown). Thereafter, the cap portion 22 is pushed downwardly to snappedly engage with the powder filled lower housing portion 14 by means of a pneumatic cap portion pushing piston 103 which is located to push from above on the cap portion 22, and another pneumatic lifting piston 104, which passes through an aperture 106 in the table top surface 78 aligned beneath the pneumatic pushing piston 102 and which ensures that the piston portion 26 of the lower housing portion 14 of the antibody testing device 16 is not forced downwardly by the action of the cap pushing piston 103. The action of the pneumatic cap portion pushing piston 103 and pneumatic lifting piston act to not only snappedly engage the cap portion 22 with the powder filled lower housing portion 14, but only to compress the powder further and bring the filter disk 18 seated on the powder in the lower housing portion 14 into contact with antibody carrying membrane 36 of the cap portion 22. In applications where a slight air gap between the antibody carrying membrane 36 of the cap portion 22 and the filter disk 18 sitting on top of the powder 20 is desired, the throw of the lifting piston 104 can be adjusted to leave the desired air gap. The snap fitting of the cap portion 22 and the lower housing portion 22 is made possible by the presence of a snap ring 38 on the upper circumference of the lower housing portion 14 and a complementary groove 39 on the inside of the cap portion 22, as best shown in FIG. 11.

Figure 9:
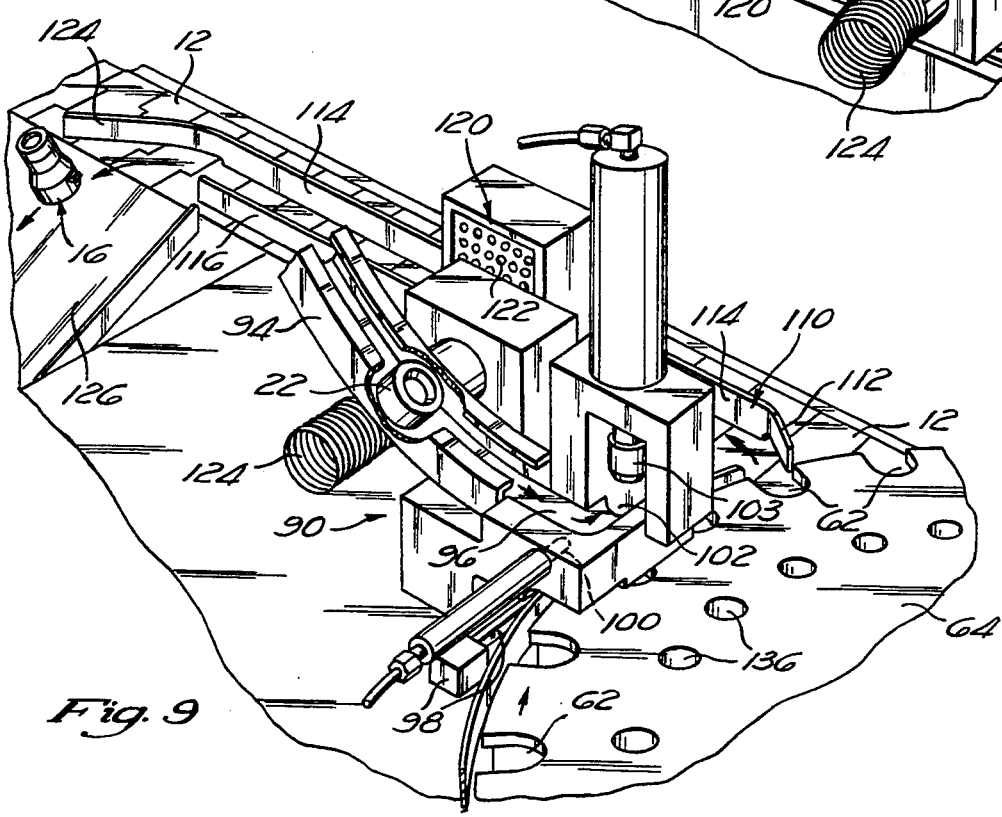
FIG. 9 is rear perspective view of the sixth station at which the antibody carrying caps are snappedly engaged with the powdered filled lower housing portions, taken along lines 9—9 of FIG. 6.

Referring to FIGS. 6 and 9, at the seventh station 110, the completely assembled antibody test device 16 (not shown) is caused to become disengaged from its slot 62 in the slotted indexing carousel wheel 64. As the fully assembled antibody test device 16 carried in a slot 62 impacts with a portion 112 of a rearwardly lying wall 114 which is angled towards the slotted indexing carousel wheel 64, the assembled antibody test device 16, is pushed free from its slot 62, and again proceeds downstream on the conveyor belt 12, between two walls 114 and 116.

Referring once more to FIGS. 6 and 9, the antibody test device 16 will pass through the eight station 120, which is a vacuuming station. At the eight station 120, the completely assembled antibody test device 16 passes on the conveyor belt 12 between two vacuum inlets 122 connected by vacuum hoses 124 to a vacuum source (not shown). This vacuuming will vacuum off any excess powder which may have accumulated on the outside of the antibody test device 16 during the prior steps.

Thereafter, the antibody test device 16 will intersect a second forwardly angled portion 124 of the rearwardly lying wall 114 which crosses the path of the conveyor belt 12 at an obtuse angle, causing the antibody test device 16 striking the portion 124 to be pushed off the conveyor belt 12 and onto a receiving tray 126 set at a decline. The completed antibody testing devices 16 will then be collected from the receiving tray 126 for packaging.

Referring to FIGS. 1 and 6, in order to insure correct alignment of the slots 62 of the slotted indexing carousel wheel 64 with each of the stations, a ninth station 130 is optionally provided. This ninth station 130 is shown as lying between the fourth station 70 and the fifth station 80, but could be located at other positions around the slotted indexing carousel wheel 64, if desired. The ninth station 130 has a pneumatically operated alignment piston 132 with a beveled head 134, which when actuated, will fit into a complementary beveled recess 136 on the slotted indexing carousel wheel 64, one each of which is axially aligned inwardly of the plurality of slots 62 on the slotted indexing carousel wheel 64. In operation, the alignment piston 132 will be engaged with a corresponding beveled recess 136 before the operations are to take place at the other stations. Thus, any slight misalignment of the slots 62 in the slotted indexing carousel wheel 64 with the stations located around the slotted indexing carousel wheel 64, such as caused by free play in the stepper motor and its gearing 66, will be corrected, ensuring smooth functioning of the apparatus 10 at each station.

Referring to FIG. 1, a control panel 138 controls the timing of the various operations taking place at the various stations, and coordinates the timing sequences so that each step is carried out at precisely the correct moment. The applicant has found that a series of mechanical cams (not shown), turned by the stepper motor and its gearing 66, which turn on and off micro switches to control air pressure feed valves of the several pneumatic pistons permit reliable functioning of the apparatus at various speeds of operation. For sake of simplicity, the slotted indexing carousel wheel 64 is shown with its slots 62 being left empty, while in actual operation, each slot 62 between stations three and seven will be occupied with portions of or completed antibody testing devices 16. Also, it should be apparent that the various assembly operations will be taking place at the various stations of the apparatus 10 concurrently, with assembly of the antibody testing devices 16 proceeding in step-like manner through each station from finish to end.

It should be borne in mind that the drawings are not rendered in actual scale so that certain features of the invention can be brought out and depicted.

The drawings and the foregoing description are not intended to represent the only form of the invention in regard to the details of this construction and manner of operation. In fact, it will be evident to one skilled in the art that modifications and variations may be made without departing from the spirit and scope of the invention. Although specific terms have been employed, they are intended in a generic and descriptive sense only and not for the purpose of limitation, the scope of the invention being delineated in the following claims:

I claim:

1. An apparatus for assembling the compounds of an antibody testing device, utilizing powder as a fluid absorbing means, into a completed antibody testing device, comprising a station at which a lower housing portion is filled with a fluid absorbing powder, a station at which a disk of filter membrane is placed on top of said liquid absorbing powder in said lower housing portion, and a station at which a membrane carrying cap portion of the antibody testing device is engaged with said lower housing portion to complete the assembling of the antibody testing device.

2. The apparatus of claim 1, wherein a station is provided to compress said liquid absorbing powder into said lower housing portion.

3. The apparatus of claim 1, where said station at which said disk of filter material is place on top of said liquid absorbing powder in said lower housing portion is located in the vicinity of a slotted indexing carousel wheel.

4. The apparatus of claim 1, wherein a vacuuming station is provided after the antibody testing device is assembled to remove any liquid absorbing powder which may have deposited on an exterior surface of said assembled antibody testing device.

5. The apparatus of claim 2, wherein said station at which said cap portions are engaged with said lower housing portions and said station at which the liquid absorbing powder is compressed are located in the vicinity of a slotted indexing carousel wheel.

6. An apparatus for assembling the components of an antibody testing device, utilizing powder as a fluid absorbing means, into a completed antibody testing device, comprising:
 (a) a first station at which a lower housing portion of the antibody testing device is placed on said apparatus;
 (b) a second station at which said lower housing portion is filled with a liquid absorbing powder;
 (c) a third station at which said housing portion is engaged with a slot on a slotted indexing carousel wheel;
 (d) a fourth station at which said liquid absorbing powder in said lower housing portion of said antibody testing device is compressed into said lower housing portion;
 (e) a fifth station at which a filter disk is placed atop said compressed liquid absorbing powder loaded in said lower housing portion;
 (f) a sixth station at which a membrane carrying cap portion of the antibody testing device is engaged with said lower housing portion to complete the assembly of the antibody testing device; and
 (g) a seventh station at which said assembled antibody testing device is disengaged from said slotted indexing carousel wheel.

7. The apparatus for assembling antibody testing devices of claim 6, wherein all stations are timed to function simultaneously, with different antibody testing devices in various states of assembly advancing in sequence through the various stations.

8. The apparatus for assembling antibody testing devices of claim 6, wherein a vacuuming station is provided to remove by vacuuming any powder which may have accumulated on the outside of said completed antibody testing device.

9. The apparatus for assembling antibody testing devices of claim 6, wherein an indexing station is provided to precisely align said slots in said slotted indexing carousel wheel with said other stations.

10. The apparatus for assembling antibody testing devices of claim 6, wherein said second station comprises a powder filling machine which delivers a predetermined quantity of a powder to said lower housing portion of said antibody testing device.

11. The apparatus for assembling antibody testing devices of claim 6, wherein said slotted indexing carousel wheel is rotated in precise steps by a stepper motor.

12. An apparatus for assembling the compounds of an antibody testing device, utilizing powder as a fluid absorbing means, into a completed antibody testing device, comprising a station at which a lower housing portion is filled with a fluid absorbing powder, a station at which a membrane carrying cap portion of the antibody testing device is engaged with said lower housing portion, and a vacuuming station at which any liquid absorbing powder which may have deposited on an exterior surface of said assembled antibody testing device is removed, to complete the assembling of the antibody testing device.

13. The apparatus of claim 12, wherein a station is provided to place a disk of filter membrane on top of said liquid absorbing powder in said lower housing portion.

14. The apparatus of claim 12, wherein a station is provided to compress said liquid absorbing powder into said lower housing portion.

15. The apparatus of claim 13, wherein said station at which said disk of filter material is placed on top of said liquid absorbing powder in said lower housing portion is located in the vicinity of a slotted indexing carousel wheel.

16. The apparatus of claim 14, wherein said station at which said cap portions are engaged with said lower housing portions and said station at which the liquid absorbing powder is compressed are located in the vicinity of a slotted indexing carousel wheel.

* * * * *